US008460259B2

(12) United States Patent
Tsai

(10) Patent No.: US 8,460,259 B2
(45) Date of Patent: Jun. 11, 2013

(54) CONTROLLED DISCHARGE OSTOMY APPLIANCE AND MOLDABLE ADHESIVE WAFER

(75) Inventor: Mingliang Lawrence Tsai, Holmdel, NJ (US)

(73) Assignee: ConvaTec Technologies, Inc., Las Vegas, NV (US)

( * ) Notice: Subject to any disclaimer, the term of this patent is extended or adjusted under 35 U.S.C. 154(b) by 42 days.

(21) Appl. No.: 13/286,774

(22) Filed: Nov. 1, 2011

(65) Prior Publication Data

US 2012/0109086 A1    May 3, 2012

Related U.S. Application Data

(60) Provisional application No. 61/409,358, filed on Nov. 2, 2010.

(51) Int. Cl.
*A61F 5/448* (2006.01)

(52) U.S. Cl.
USPC ........... 604/335; 604/317; 604/332; 604/337; 604/338; 604/339; 604/340; 604/341; 604/342; 604/343; 604/344

(58) Field of Classification Search
None
See application file for complete search history.

(56) References Cited

U.S. PATENT DOCUMENTS

| 5,549,588 | A * | 8/1996 | Johnsen | 604/339 |
|---|---|---|---|---|
| 6,071,268 | A * | 6/2000 | Wagner | 604/332 |
| 6,659,988 | B1 * | 12/2003 | Steer et al. | 604/333 |
| 6,689,111 | B2 * | 2/2004 | Mulhauser et al. | 604/332 |
| 2003/0100870 | A1 * | 5/2003 | Villefrance | 604/333 |
| 2003/0187393 | A1 * | 10/2003 | Cline | 604/131 |
| 2004/0006320 | A1 | 1/2004 | Buglino | |
| 2004/0193122 | A1 | 9/2004 | Cline | |
| 2005/0054997 | A1 * | 3/2005 | Buglino et al. | 604/332 |
| 2006/0184145 | A1 * | 8/2006 | Ciok et al. | 604/338 |
| 2006/0200101 | A1 * | 9/2006 | Mullejans et al. | 604/339 |
| 2006/0206069 | A1 * | 9/2006 | Cline | 604/337 |
| 2007/0088300 | A1 * | 4/2007 | Cline et al. | 604/342 |
| 2007/0123832 | A1 * | 5/2007 | Cline et al. | 604/335 |
| 2007/0191794 | A1 * | 8/2007 | Cline et al. | 604/335 |
| 2008/0269698 | A1 * | 10/2008 | Alexander et al. | 604/332 |
| 2009/0157140 | A1 * | 6/2009 | Martino et al. | 607/41 |
| 2010/0121291 | A1 * | 5/2010 | Davies et al. | 604/333 |
| 2010/0241092 | A1 * | 9/2010 | Nguyen-DeMary et al. | 604/336 |
| 2011/0040269 | A1 * | 2/2011 | Cline | 604/335 |
| 2012/0179124 | A1 * | 7/2012 | Nguyen-Demary et al. | 604/333 |

FOREIGN PATENT DOCUMENTS

| WO | 2009029610 | 3/2009 |
|---|---|---|
| WO | 2010060116 | 5/2010 |

* cited by examiner

*Primary Examiner* — Melanie Hand
*Assistant Examiner* — Andrew S Lo

(57) ABSTRACT

A controlled discharge ostomy appliance is described for use with an adhesive body fitment. The body fitment comprises an adhesive wafer having a stomal aperture that is manually shapeable by folding or rolling back a rim portion of the adhesive around the stomal aperture.

29 Claims, 7 Drawing Sheets

CONTROLLED DISCHARGE OSTOMY APPLIANCE AND MOLDABLE ADHESIVE WAFER

FIELD OF THE INVENTION

The present invention relates to a controlled discharge ostomy appliance, in particular with a stoma occluding seal.

BACKGROUND OF THE INVENTION

US-A-2004/193122 describes examples of controlled discharge ostomy appliance including a seal that is urged against the exterior surface of a stoma. The stoma seal is carefully designed and supported so as to cooperate with the stoma tissue to form an occlusive, non-entrant seal. The seal obstructs discharge of liquid and/or solid body waste, while permitting flatus to escape along the interface between the seal and the stoma, and vent around the seal periphery to a dedicated flatus vent of the appliance. The appliance is removably attached to a body-side mounting wafer. A distensible waste collector is deployed when the appliance (with its seal) is removed from the body-side mounting wafer, to provide a closed collection space for body waste that may discharge spontaneously. The adhesive has a fixed size stomal aperture and an elastomeric seal extends peristomally between the adhesive and stoma, against which the stoma seal may also bear.

US-A-2004/006320 describes a different type of body-mounting wafer, normally for ostomy pouches, and including a stomal aperture that is manually moldable. Such a mounting wafer offers many advantages, especially ease of use and custom adaptation to each ostomate's unique size and shape of stoma. The adhesive wafer is flexible and includes exposed adhesive on both its skin-facing surface and its opposed non-skin-facing surface. The stomal aperture is manually moldable by rolling or folding back the rim of the adhesive wafer around the stomal aperture, into adhesive contact with its non-skin-facing surface. The adhesive contact anchors the adhesive wafer in its new shape around the stomal aperture. Despite the potential advantages, this type of moldable mounting wafer is generally incompatible with the aforementioned controlled discharge device. The presence of a rolled-back adhesive rim, with an exposed adhesive surface facing the seal, interferes with the carefully designed seal operation. In particular, the seal is vulnerable to adhering against the exposed adhesive surface of the wafer, either immediately on contact, or over time while the appliance is worn. The risk of adhesion can increase over time, because the moist environment at the stoma seal progressively softens the adhesive making it tackier. Adhesion of the seal to the rolled back adhesive rim in the wafer creates a closed system, which traps flatus at the stoma seal instead of permitting intended escape of flatus around the periphery of the seal. The pressure of trapped flatus may (i) weaken the seal allowing effluent to leak to the adhesive, (ii) weaken the adhesion of the wafer to the skin, (iii) risk the appliance separating unintentionally.

WO-A-2009/029610 describes a refined seal support for a controlled discharge device using resilient foam, and a fluid damper chamber, for controlling the seal force and position as the stoma changes dynamically while the appliance is worn. The seal combines flatus venting around the periphery of the seal, with ability for the seal to advance and retract adaptively to avoid prolonged application of excessive pressure on the stoma. However, the carefully designed operation of the seal would also be compromised if used with a moldable adhesive wafer of the type described in US-A-2004/006320 above. In addition to trapping flatus in the same manner as explained above, adhesion of the stoma seal to the exposed adhesive holds the seal captive to the adhesive wafer instead of the seal being able to advance and retract adaptively.

The present invention addresses at least some of the above issues.

SUMMARY OF THE INVENTION

Broadly speaking, one aspect of the invention is the provision of a controlled discharge ostomy appliance that is removably attachable to a body mounting device. The appliance comprises a stoma seal facing towards the stoma in use. The stoma seal comprises a first (inner) seal wall, and a second (outer) seal wall. The first seal wall has a seal face for contacting the stoma through an aperture (seal-contact aperture) in the second seal wall. The second seal wall overlaps a portion (e.g. a peripheral portion) of the seal face of the first seal wall.

When used with a body mounting device having (at least when in use) an exposed adhesive surface region facing towards the stoma seal, the second seal wall acts as a shield or separator layer preventing substantial adhesive engagement between the first seal wall and the exposed adhesive. Even if the second seal wall is adhesively engaged by the exposed adhesive of the wafer, and held captive by the adhesive engagement, this does not affect substantially the seal of the seal face of the first seal wall against the stoma.

In one form, a gas vent passage is provided by the interface between the first and second walls, to allow flatus at the seal face and/or seal-contact aperture to vent away from the seal via this vent passage. Flatus escaping the stoma at the seal face in the region of the seal-contact aperture may vent peripherally via the vent passage defined by the interface between the first and second walls. The vent passage may be defined by a clearance between the walls. Preferably the vent passage comprises one or more exits for permitting flatus that has entered between the first and second seal walls to escape at a position spaced from the seal-contact aperture. For example, at least one of the seal walls may include at least one flatus vent aperture positioned away from the seal-contact aperture. Alternatively, one or more spaces or discontinuities may be provided in a mounting joint (e.g. a joint between the first and second seal walls).

Additionally or alternatively, at least a portion of the seal face of the first seal wall overlapped by the second seal wall is able to displace relative to the second seal wall. The first seal wall can reposition to maintain a desired seal pressure against the stoma, independently of adhesion of the second seal wall to the body mounting wafer. If the degree or extent of protrusion of the stoma increases, the first seal wall is able (with a suitable force characteristic) to retract slightly into the appliance to accommodate the increased protrusion, despite any adhesion of the second seal wall to the body mounting wafer.

The first and second seal walls may be formed from different pieces of material (optionally attached together), or the first and second seal walls may be portions of the same piece of material (e.g. folded to define a desired configuration.)

Optionally, the same appliance may be configured to be useable with a body fitment that has only a non-adhesive surface facing towards the stoma seal (for example, a non-moldable adhesive type). The stoma seal can work equally well. With this option, the ability of the appliance to be used with either type of body fitment is advantageous both to ostomates (so that an individual ostomate can use either or both types of body fitment according to his or her preference, or according to which type of body fitment the ostomate currently has available) and to manufacturers/suppliers (by enabling the number of different models and inventory to be reduced).

Additionally, the same appliance may be configured to be useable with a body fitment and with the use of ostomy accessories such as adhesive powder, adhesive paste, or peristomal seal (i.e., Eakin® Cohesive Seal, marketed by TG Eakin Limited in UK). The purpose of these adhesive accessories is to protect the peristomal skin. However, the adhesive nature of these adhesive accessories in use with and without a body fitment system presents a challenge for the stoma seal without the second seal wall as a shield. With the second seal wall described in this invention, the stoma seal can work equally well. With this option, the ability of the adhesive accessories to be used with either type of body fitment is advantageous both to ostomates (so that an individual ostomate can use either or both types of body fitment according to his or her preference, or according to which type of body fitment the ostomate currently has available) and to manufacturers/suppliers (by enabling the number of different models and inventory to be reduced).

In one form, the first and second seal walls have corresponding shapes, nested one within the other. Merely by way of example, the first and second seal walls may have generally U-shape, or a top-hat shape with or without a flange. In another form, the first and second seal walls have different shapes. For example, the first seal wall may have a U-shape or top-hat shape with or without a flange. The second seal wall may have a generally planar shape, e.g. washer or annular disc shape.

In a related aspect, the invention comprises a controlled discharge ostomy appliance for use with an adhesive body fitment. The body fitment comprises an adhesive wafer having a stomal aperture that is manually shapeable by folding or rolling back a rim portion of the adhesive around the stomal aperture. At least after shaping, the adhesive presents an exposed adhesive surface portion facing towards the controlled discharge ostomy appliance. The appliance comprises a stoma seal, urged towards the stomal aperture of the wafer for sealing against a stoma in use. The stoma seal comprises a first seal wall and a second seal wall. The second seal wall has a seal-contact aperture therein, and the first seal wall has a stoma contact face for containing a stoma, in use, through the seal-contact aperture of the second seal wall. The second seal wall shields the first seal wall to obstruct the first seal wall adhering to the exposed adhesive surface portion of the wafer facing towards the controlled discharge ostomy appliance.

Additional objects, features and advantages of the invention will become apparent from the following description of preferred embodiments. Protection may be sought for any novel feature or idea disclosed herein and/or illustrated in the drawings, whether or not emphasis has been placed thereon.

DETAILED DESCRIPTION OF PREFERRED EMBODIMENT

Figure 1:
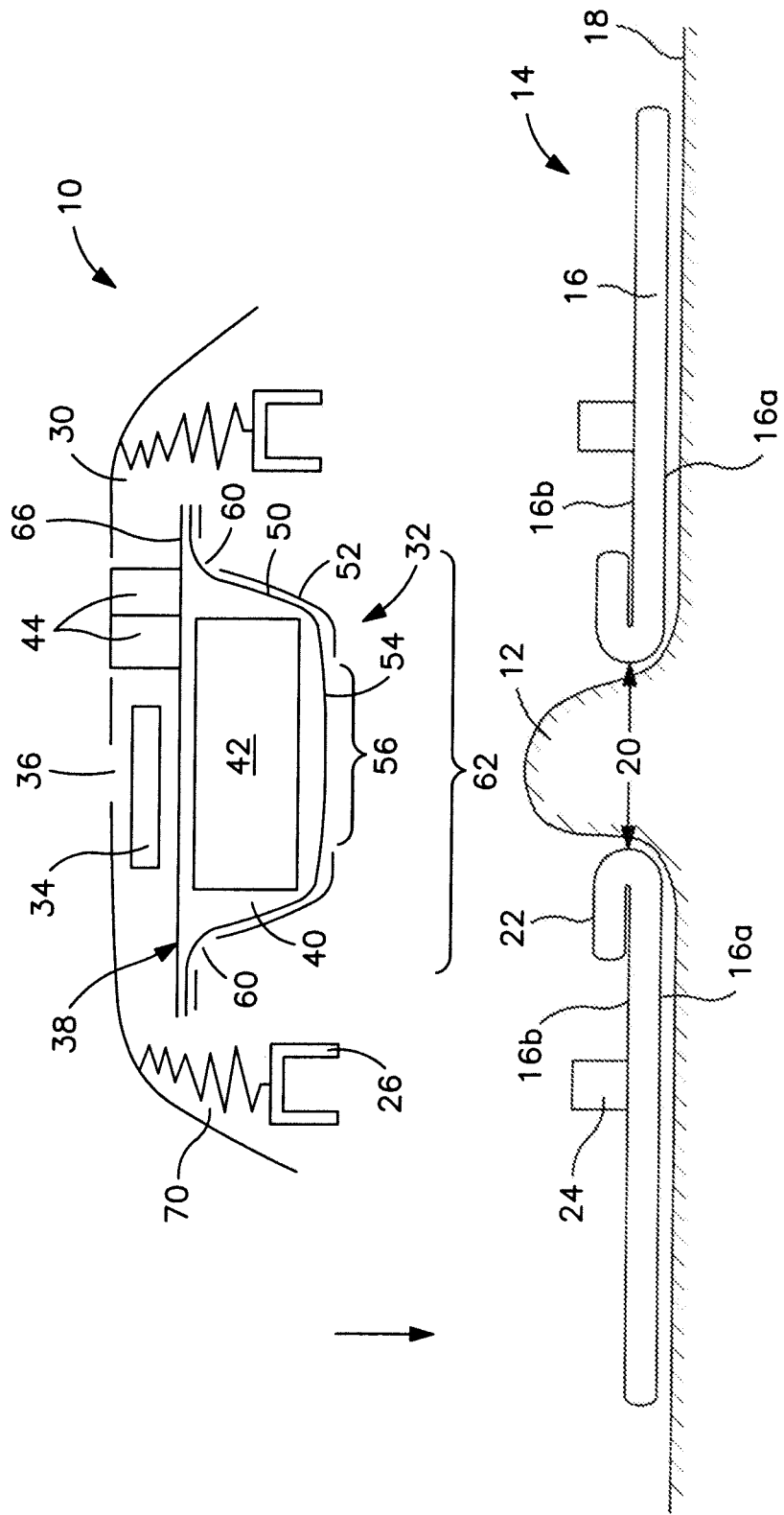
FIG. 1 is a schematic cross-section through a moldable body fitment adhered to the site of a stoma, and a controlled discharge appliance prior to mounting on the body fitment.

Referring to the drawings, a controlled discharge ostomy appliance 10 is illustrated for fitting to the body at a stoma 12 using a body fitment 14. The illustrated embodiment of appliance 10 is suitable as being universally useable either with a moldable type of body fitment 14 (FIGS. 1 and 2), or a non-moldable type of body fitment (not shown).

Figure 2:
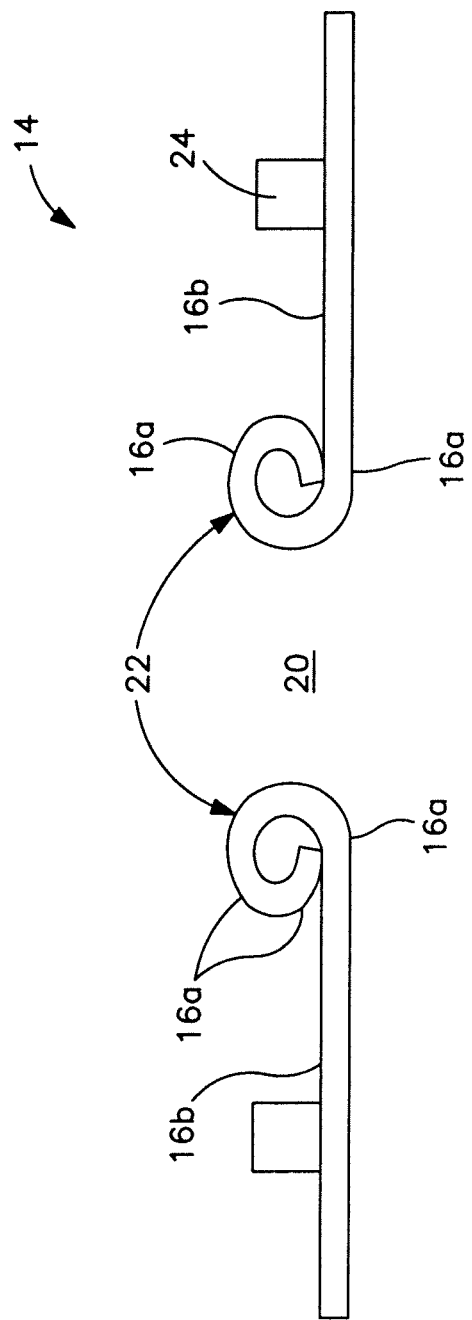
FIG. 2 is a schematic cross-section through a second example of moldable body fitment.

Referring to FIGS. 1 and 2, the moldable body fitment 14 comprises a wafer 16 (or pad) of medical-grade skin-compatible adhesive for adhesion to an ostomate's peristomal skin 18. The wafer includes a skin-facing (or skin-contacting) adhesive surface 16a, and an opposite non-skin facing (or non-skin-contacting) surface 16b. At least a portion of the non-skin-facing surface 16b may be adhesive (FIG. 1), or it may be non-adhesive (FIG. 2). A stomal aperture 20 of the wafer 16 is manually moldable or shapeable by folding or rolling back a rim portion 22 of adhesive around the aperture 20 to define a desired size and shape of aperture 20 to suit the individual stoma 12. In the example of FIG. 1, the rim portion 22 is folded back into direct contact with the exposed adhesive of the non-skin-facing surface 16b. The contact with the adhesive non-skin-facing surface 16b anchors the adhesive in its new shape. Such an arrangement is similar to that described in the aforementioned US-A-2004/006320. In the example of FIG. 2, the rim portion 22 is rolled back through at least 360 degrees, so that a portion of the skin-facing surface 16a now faces the non-skin-contacting surface 16b to enable the adhesive anchoring. In either case, the wafer 16 includes an exposed adhesive surface around the stomal aperture 20, either initially and/or as a result of molding. In the particular forms shown, manual molding creates a relatively raised region of exposed adhesive where the rim portion 22 is folded back.

Although not illustrated, the skin-facing surface 16a of the wafer 16 (FIGS. 1 and 2) may initially be covered by a removable release sheet, for example, comprising or carrying silicone. The release sheet serves to protect the skin-facing surface 16a prior to use, and to prevent unintended adhesion. Additionally or alternatively, in the form illustrated in FIG. 1, the exposed adhesive portion of the non-skin-facing surface 16b may also be covered by such a removable release sheet prior to use.

The body fitment 14 further comprises a body-side coupling element 24 for coupling to an appliance-side coupling element 26 of the appliance 10 for coupling the appliance 10 to the body fitment 14. In the present embodiment, the coupling elements 24 and 26 are configured to form a mechanical interference fit (e.g. interlock). For example, one of the coupling elements 24 comprises an annular rib, and the other coupling element 26 comprises an annular channel for receiving the rib to mate therewith. In alternative embodiments, different mechanical or non-mechanical (e.g. adhesive) couplings may be used as desired.

The appliance 10 comprises a housing 30 containing a seal (stoma seal) 32 for bearing against the stoma 12 in use to obstruct discharge of solid and/or liquid body waste. The stoma seal 32 is configured to allow escape of flatus, which is vented along a gas flow path through a deodorizing filter 34 to an atmospheric vent 36. The appliance 10 comprises a seal support 38 for urging the stoma seal 32 towards the stoma 12 in use. Different forms of support 38 are possible. For example, the support 38 could be inflatable or pressurizable (e.g. sustain pressure permanently or temporarily), and/or it could comprise a resilient member. In the preferred form, the support comprises a combination of fluid containing chamber 40 and a resilient member 42 (optionally positioned within the chamber 40). The resilient member 42 urges the stoma seal 32, and the fluid-containing chamber 40 acts as a (e.g. pressurizable) fluid-damper to resist or slow at least certain displacement of the stoma seal 32. One or more fluid-transfer ports 44 control entry and exit of fluid (e.g. air) with respect to the chamber 40 to define the fluid-damping effect. The function of the support 38 is to maintain a desired seal pressure of the stoma seal 32 against the stoma 12, while permitting the stoma seal 32 to adopt a suitable position for contacting the stoma 12. The position of the stoma seal 32 may vary during use, for example, to adapt to increased and/or decreased protrusion of the stoma 12, body movements and different positions adopted by the ostomate, passage of flatus, accumulation of stool behind the stoma. The fluid-damping effect may allow the seal pressure to increase temporarily, in response to an outward pressure challenge from the stoma 12, while permitting the seal position to adapt over time to avoid excessive pressure being applied for a prolonged period. The resilient member 42 may be of resiliently compressible foam. A surface of the resilient member 42 nearest to the portion of the stoma seal 32 facing the stoma 12 may include one or more corrugations, undulations, projections, channels, or other non-flat surface features to promote flatus escape towards the periphery of the stoma seal 32.

The stoma seal 32 comprises a first (inner) seal wall 50 and a second (outer) seal wall 52. The terms "inner" and "outer" may refer to proximity to the seal support 38. The first seal wall 50 includes a stoma-contacting seal face 54 configured for contacting the stoma 12 in use through a stoma-contact aperture 56 of the second seal wall 52. The second seal wall 52 covers a peripheral portion of the seal face 54. The first seal wall 50 optionally forms part of a wall defining the chamber 40.

Figure 3:
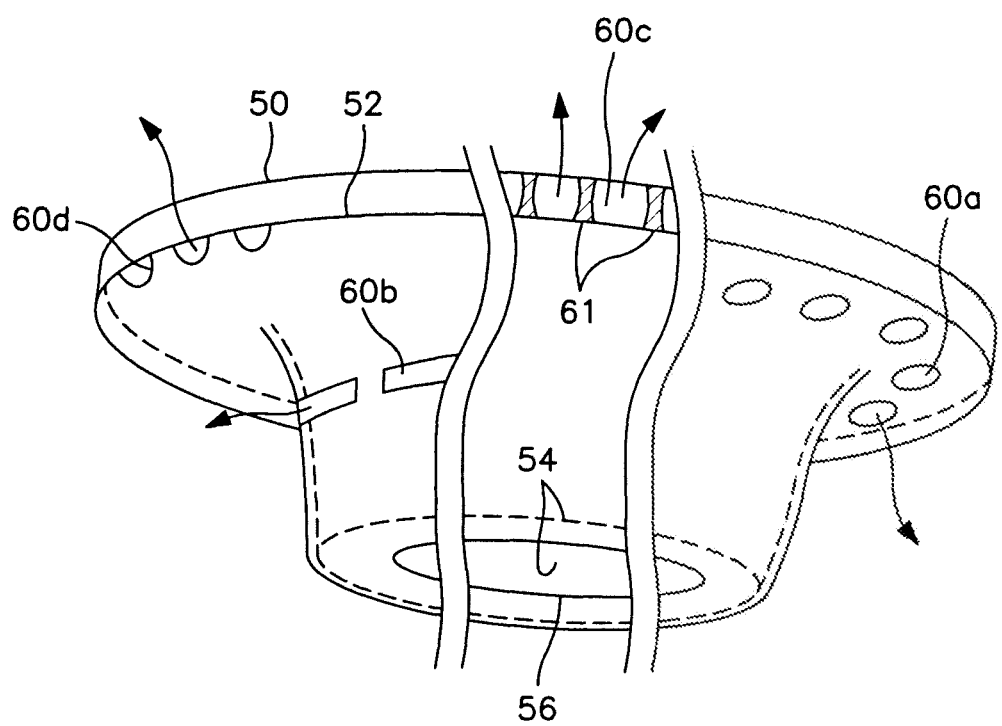
FIG. 3 is a schematic underside perspective view showing the stoma seal in various examples.
Figure 4:
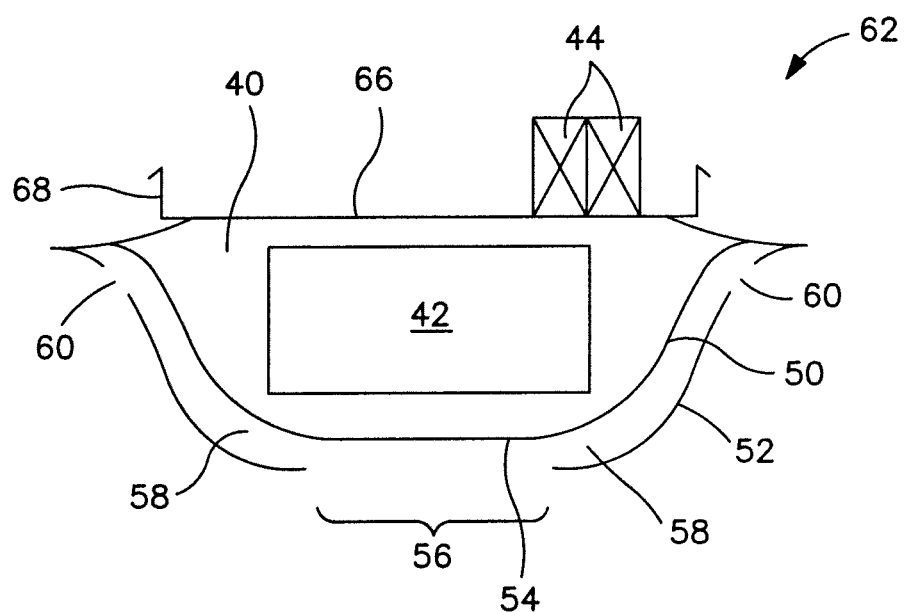
FIG. 4 is a schematic section showing the stoma seal module in isolation.
Figure 5:
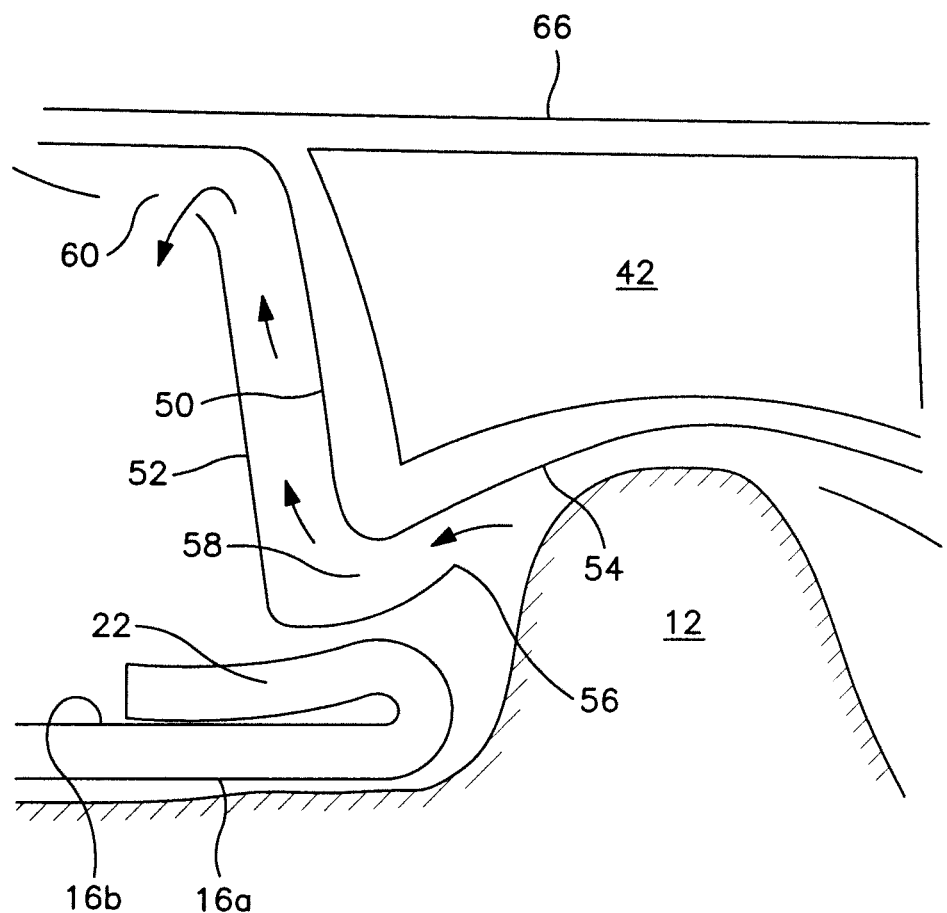
FIG. 5 is a partial, enlarged schematic section similar to FIG. 1, but showing the controlled ostomy device mounted to the body fitment. In this figure, certain surfaces are shown separated for ease of identification, but it will be understood that in use the surfaces are pressed one against another.
Figure 6:
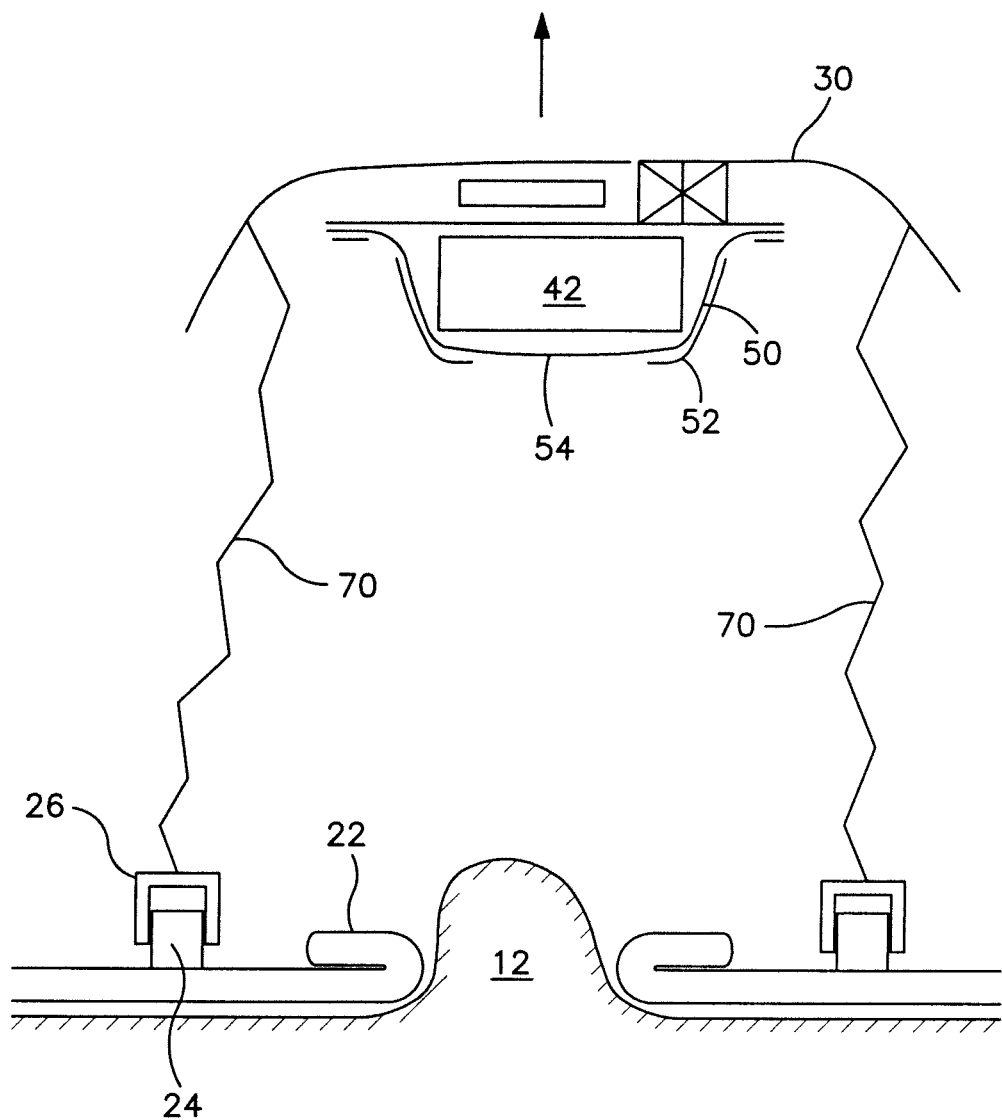
FIG. 6 is a schematic section showing a first stage of removal of the appliance after use, including distension of the waste collector.

A gas vent passage 58 is provided by the interface between the first and second seal walls 50 and 52, to allow flatus at the seal face 54 and/or seal-contact aperture 56 to vent away from the seal via the vent passage 58 to an exit at 60 in FIG. 4. Referring to FIG. 6, even if the second (outer) seal wall 52 is adhesively engaged by the rim portion 22 and becomes captive with respect to the rim portion 22, this does not interfere with the ability of flatus to vent away. As explained previously, the second seal wall 52 may become attached to the exposed adhesive surface ether immediately, or progressively over time. The risk of adhesion can increase over time, because the moist environment at the stoma seal progressively softens the wafer adhesive making it tackier. With the present embodiment, flatus escaping the stoma 12 at the seal face 54 in the region of the seal-contact aperture 56 may vent peripherally via the vent passage 58. The vent passage 58 may be defined by a clearance between the walls 50 and 52. Preferably the vent passage comprises one or more exits 60 for permitting flatus that has entered between the first and second seal walls to escape at a position spaced from the seal-contact aperture. For example, at least one of the seal walls may include at least one flatus vent aperture 60 positioned away from the seal-contact aperture. For example, in FIG. 3, apertures 60a may be provided in a peripheral flange portion of the second seal wall 52, and/or apertures 60b may be provided in a side wall portion of the second seal wall 52. Additionally or alternatively, one or more spaces or discontinuities 60c may be provided in a mounting joint, for example, a joint 61 between the first and second seal walls in FIG. 3 and in FIG. 7 described later. The joint 61 may be defined by a series of spaced apart spot welds. Additionally, apertures 60d can be created at the seal area between the first seal film 50 and the second seal film 52. Such an arrangement allows the apertures to be created more easily because they are further removed in the flange area of the seal.

The first and second seal walls 50 and 52 are made of flexible material, preferably plastics, more preferably plastics film. At least the first seal wall 50 (and preferably also the second seal wall 52) is made of material that is substantially impermeable to flatus, liquid and solid stool. Example materials include polyetheylene (homopolymer or copolymer), polypropylene, ethylene vinyl acetate, synthetic rubber, nylon, polyester, etc. Conventional ostomy pouch film based on a multi-layer construction of poly(vinylidene chloride) and ethylene vinyl acetate is also a candidate material. The first and second seal walls 50 and 52 may be made of the same material or of different materials. The first and/or second seal wall may be thermoformed to have a flexible three-dimensional shape. The thickness of the first and second seal walls 50 and 52 may be the same or different. The primary function of the second seal wall is to act as a shield. As long as the second seal has sufficient strength, it is preferred for the second seal to be thin and soft. A thin and soft edge near the aperture would be safe and friendly towards the stoma when stoma and the edge of second seal are in close proximity. Additionally, the edge of the second seal 52 near the aperture 56 may be beveled. Such a soft edge feature could be made in the same thermoforming step when the second seal is made into a U-shape in order to be coupled over the first seal 54.

The provision of the second seal wall 52 does not add significantly to the complexity of the appliance, nor does the addition of the second seal wall 52 occupy significant space compared to a single (inner) seal wall 50. This is especially important in the illustrated embodiment, where it is desirable to maintain a compact construction, with elements accommodated within a relatively confined space, and achieving desirable low profile height compared to the skin surface.

Referring to FIGS. 1-5, the first and second seal walls 50 and 52 are in the present embodiment joined to each other only at one or more positions spaced (laterally and/or axially) from the periphery of the seal-contact aperture 56 by at least at least 5 mm. Such spacing enables the first seal wall 50 to be capable of limited movement or displacement independently of the second seal wall 52. Additionally, the first seal wall 50 and the second seal wall 52 can be joined together at the base of the flange shown in FIG. 3. This arrangement would then allow full opening between the first seal wall 50 and the second seal wall 52 near the aperture 56. The first seal wall 50 is able to adopt a suitable position to contact the stoma 12, and to retract towards the housing 30, or advance towards the skin 18, in dependence on changes in stoma protrusion. If, for example, the stoma 12 pushes outwardly with an increased force against the stoma seal 32, the seal support 38 may, with a suitable delay defined by the fluid-damping, progressively relax to permit the stoma seal 32 to retract into the appliance and avoid excessive force applied on the stoma 12 for a prolonged period. The first seal wall 50, contacting the stoma 12 through the seal-contact aperture 56, is able to retract despite the second seal wall 52 being captively engaged by the adhesive wafer 16 and prevented from retracting.

The stoma seal 32 (made of the walls 50 and 52) and the support 38 (including the fluid-containing chamber 40, the resilient member 42 and the ports 44) together may form part of a seal unit or module 62, shown in isolation in FIG. 4. The seal module 62 is a generally integral construction unit, one of two or more modules from which the appliance 10 can easily be assembled. The first and second seal walls 50 and 52 generally have the same configuration, for example, a top-hat shape including a base flange. The three-dimensional shape may, for example, be imparted by thermoforming flexible plastics film. The walls 50 and 52 are nested one within the other. The flanges of the walls 50 and 52 are sealed, for example, welded, to a carrier film 64, optionally at a common seam, or respective adjacent or spaced seams. The carrier film is sealed, e.g. welded or adhered, to a support wall 66 which is substantially rigid and/or more rigid than the walls 50 and 52. The structure defines the fluid-containing chamber 40, and the resilient member 42 is arranged within the chamber 40 during manufacture. An example resilient member 42 is resilient foam. The support wall 66 carries the one or more fluid-transfer ports 44 communicating with the chamber 40. The support wall 66 optionally carries or comprises one or more clips or fixings 68 for attaching the seal module 62 to another portion of the appliance 10.

In the illustrated example, the appliance 10 further comprises a waste collector 70. The waste collector 70 may be generally tubular or bag-shaped, with openings at opposite end portions. One end of the waste collector 70 is coupled to the appliance-side coupling element 26, and the other end is coupled to the housing 30. The appliance-side coupling element 26 is additionally coupleable directly to the housing 30. The coupled state defines a first operation state of the appliance 10, in which the waste collector 70 is collapsed to a compact annular form, and stowed within the housing. This is the form in which the appliance 10 is initially provided and used.

The seal module 62 is preferably receivable within the space defined by the waste collector 70. The seal module 62 may be attached by the fixings 68 to the portion of the housing encircled by the waste collector 70. A space may be reserved between the inner surface of the housing 30 and the outer surface of the support wall 66, for receiving the deodorizing filter 34. Flatus exiting the stoma seal 32 via the apertures 60 can therefore enter the space defined by the collapsed collector 70, and from there pass behind the support wall 38 and through the deodorizing filter to the atmospheric vent. The apertures 60 may be relatively large, for example, each at least 4 mm in diameter. The apertures 60 collectively may define an open area of at least 10 mm² and may exceed 100 mm². Use of relatively large aperture size and/or area can reduce risk of blockage by the material of the collapsed waste collector 70 in the confined space of the appliance 10. Aperture 60 could also take the form of a slit or a discontinuity in a joint between the seal walls.

Referring to FIG. 6, when it is desired to remove the appliance 10, the housing 30 is manipulated in order to detach the housing 30 from the appliance-side coupling element 26, without (at this stage) separating the appliance-side coupling element 26 from the body-side coupling element 24. Pulling away the housing 30 distends the waste collector 70. The seal module 62 is attached to the housing 30, and so the pulling away of the housing similarly pulls the stoma seal 32 clear of the stoma. If the second (outer) seal wall 52 is adhesively engaged by the exposed adhesive surface of the rim portion 22 of the wafer 16, the pulling away of the stoma seal 32 automatically pulls or peels the second seal wall 52 from the adhesive engagement. With the stoma seal 32 clear of the stoma 12, any body waste accumulated at the stoma 12 is free to discharge into the waste collector 70, without obstruction.

The provision of the second seal wall 52 as part of the stoma seal 32 that is removed with the housing 30, rather than remaining as gasket partly covering the stoma, therefore avoids any obstruction or risk of diversion of body waste discharging from the stoma.

Following the discharge of accumulated body waste into the collector 70, the appliance-side coupling element 26 may be separated from the body-side coupling element 24, allowing complete removal and disposal of the appliance and its collected effluent.

Figure 7:
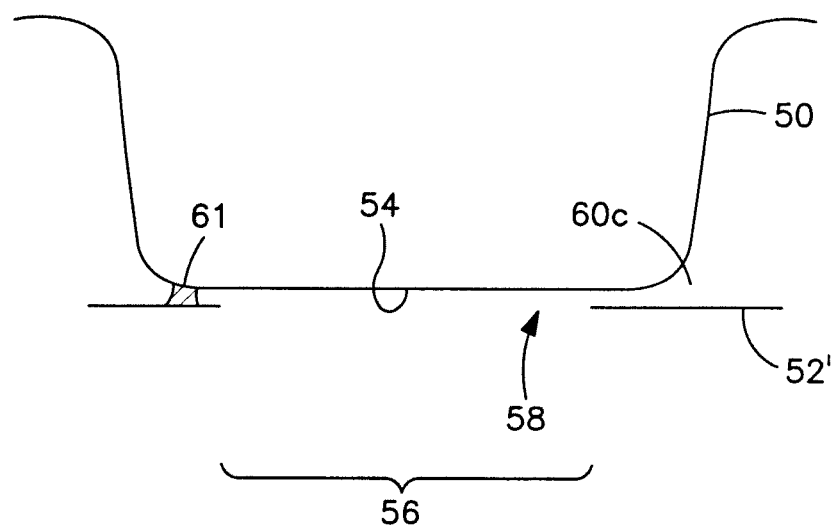
FIG. 7 is a schematic section showing a further example of stoma seal.

FIG. 7 illustrates an alternative example of stoma seal comprsing first and second walls 50 and 52'. The first seal wall 50 is similar to that described above, having a top-hat shape. The second seal wall 52' has a different shape and/or configuration from the first seal wall 50. The second seal wall 52' optionally is generally planar, for example in the form of a washer or annular disc. The second seal wall 52' defines a seal contact aperture 56 in a similar manner to that described previously. A vent passage 58 is defined between the first and second seal walls 50 and 52'. Flatus can escape peripherally via exit clearances or discontinuities 60c in a weld joint 61 between the first and second seal walls 50 and 52'. The weld joint 61 may take the form of spaced spot welds or spaced adhesive regions.

The embodiment of FIG. 7 provides the same venting of flatus as the first embodiment, even if the second seal wall 52' is adhesively engaged by the body wafer 16.

It will be appreciated that the provision of a second (outer) seal wall as illustrated in the preferred embodiments can provide important advantages by enabling a non-entrant occluder seal to be used with a type (e.g. moldable) of body fitment having exposed adhesive facing the stoma seal, without interfering with the operation of the seal. The design of the stoma seal 32 using inner and outer walls 50 and 52 may optionally be usable for a mounting device that does not have exposed adhesive facing towards the stoma seal 32 around the stomal aperture 20. For example, the non-skin-facing surface 16b of the adhesive wafer 16 is non-adhesive (for example, it is covered by a non-adhesive backing material, which may optionally be a plastics film). The first and second seal walls 50 and 52 may function together as a single, combined seal wall that can be repositioned dynamically according to the degree of protrusion of the stoma 12, and the force applied/supported by the seal support 38. Flatus may escape at the periphery of the contact between the stoma seal 32 and the stoma 12 and/or flatus may escape along the interface 58 between the inner and outer seal walls 50 and 52 in the same manner as described above.

The moldable body fitment 14 can be a separate appliance from the controlled discharge ostomy appliance 10, which is commonly called as a two-piece ostomy device. Additionally, the moldable body fitment 14 and the controlled discharge ostomy appliance 10 can be one-unit, which can be joined together by a flexible flap with or without the rigid coupling elements 24 and 26 to create a mechanical interference fit (e.g. interlock). This becomes a one-piece ostomy appliance which has a moldable adhesive. An adhesive coupling feature can be used to replace the rigid coupling elements 24 and 26. This becomes a one-piece ostomy appliance which has a moldable adhesive.

It will also be appreciated that the foregoing description is directed to a preferred embodiment of the invention. Many modifications, improvements and equivalents may fall within the scope of any allowed claims.

The invention claimed is:

1. A controlled discharge ostomy appliance comprising:
   a housing;

a stoma seal comprising a first seal wall and a second seal wall, the second seal wall having a seal-contact aperture therein, and the first seal wall having a stoma contact face for containing a stoma, in use, through the seal-contact aperture of the second seal wall;

a seal support for urging the stoma seal towards a stoma.

2. The controlled discharge ostomy appliance of claim 1, wherein the second seal wall overlaps a peripheral region of the stoma contact face of the first wall.

3. The controlled discharge ostomy appliance of claim 1, wherein the aperture of the second seal wall is smaller than the size of the stoma contact face of the first seal wall.

4. The controlled discharge ostomy appliance of claim 1, further comprising a flatus vent passage at the interface between the first seal wall and the second seal wall for permitting passage of flatus therethrough.

5. The controlled discharge ostomy appliance of claim 4, further comprising at least one exit spaced from the seal-contact aperture for permitting flatus entering the flatus vent passage at the seal-contact aperture to escape via the exit.

6. The controlled discharge ostomy appliance of claim 5, wherein the at least one exit is selected from: a clearance between the seal walls; an aperture in the second seal wall; a discontinuity in a joint between the seal walls; and a slit in the second seal wall.

7. The controlled discharge ostomy appliance of claim 1, wherein the contact face of the first seal wall is displaceable relative to the aperture of the second seal wall.

8. The controlled discharge ostomy appliance of claim 1, wherein the first seal wall is attached relative to the second seal wall only at one or more regions spaced away from the aperture.

9. The controlled discharge ostomy appliance of claim 5, wherein said spacing is at least 5 mm from the periphery of the aperture.

10. The controlled discharge ostomy appliance of claim 1, wherein the first and second seal walls have the same general configuration.

11. The controlled discharge ostomy appliance of claim 10, wherein the configuration is selected from top-hat shaped with a flange; and top-hat shaped without a flange.

12. The controlled discharge ostomy appliance of claim 1, wherein the first and second walls nest one within the other.

13. The controlled discharge ostomy appliance of claim 1, wherein the first and second seal walls have substantially different shapes.

14. The controlled discharge ostomy appliance of claim 1, wherein the second seal wall has a washer shape.

15. The controlled discharge ostomy appliance of claim 1, wherein the seal support comprises a resilient member for urging the stoma seal towards the stoma.

16. The controlled discharge ostomy appliance of claim 15, wherein the seal support further comprises a fluid-containing chamber, and at least one fluid-transfer port for controlling fluid-flow with respect to the chamber, to define a fluid-damping characteristic for the seal support.

17. The controlled discharge ostomy appliance of claim 16, wherein the first seal wall defines at least a part of a wall of the fluid-containing chamber.

18. The controlled discharge ostomy appliance of claim 1, further comprising a waste collector, the waste collector being distensible and bounding an interior space of the appliance, wherein the first and second seal walls are received within said interior space bounded by the waste collector.

19. In combination:
a controlled discharge ostomy appliance; and
an adhesive body fitment for mounting the controlled discharge ostomy appliance at a stoma,
wherein:
the adhesive body fitment comprises an adhesive wafer having a stomal aperture that is manually shapeable by folding or rolling back a rim portion of the adhesive around the stomal aperture and, at least after shaping, the adhesive presents an exposed adhesive surface portion facing towards the controlled discharge ostomy appliance; and
the controlled discharge ostomy appliance comprises a stoma seal, urged towards the stomal aperture of the wafer for sealing against a stoma in use, the stoma seal comprising a first seal wall and a second seal wall, the second seal wall having a seal-contact aperture therein, and the first seal wall having a stoma contact face for contacting a stoma, in use, through the seal-contact aperture of the second seal wall, the second seal wall being configured to shield the first seal wall to obstruct the first seal wall adhering to said exposed adhesive surface portion of the wafer facing towards the controlled discharge ostomy appliance.

20. The combination of claim 19, wherein the adhesive wafer has an adhesive skin-facing surface and an adhesive non-skin-facing surface portion.

21. The combination of claim 19, wherein the controlled discharge ostomy appliance comprises a waste collector, the waste collector being distensible and bounding an interior space of the appliance, wherein the first and second seal walls are received within said interior space bounded by the waste collector.

22. The combination of claim 19, wherein the controlled discharge ostomy appliance and the adhesive body fitment for mounting the controlled discharge ostomy appliance at a stoma are two separate appliances.

23. The combination of claim 19, wherein the controlled discharge ostomy appliance and the adhesive body fitment for mounting the controlled discharge ostomy appliance at a stoma are one unit.

24. A seal unit for use in a controlled discharge ostomy appliance, the seal unit comprising:
a fluid-containing chamber defined at least partly by a flexible first seal wall, the first seal wall having a seal face for contacting a stoma in use;
a resilient member received within the fluid-containing chamber;
a flexible second seal wall covering a portion of the first seal wall to shield the first seal wall, the second seal wall having a seal-contact aperture therein exposing at least a portion of the seal face of the first seal wall, such that, in use, the seal face of the first seal wall contacts a stoma through the seal-contact aperture of the second seal wall.

25. The seal unit of claim 24, further comprising at least one flatus vent passage between the first and second seal walls.

26. The seal unit of claim 24, wherein the first and second seal walls are attached with respect to each other at a location spaced from the seal contact-aperture.

27. In combination:
a controlled discharge ostomy appliance; and
an adhesive accessories to be applied at peristomal skin around a stoma which would allow direct contact of adhesive accessories with the controlled discharge ostomy appliance at a stoma,
wherein:
the controlled discharge ostomy appliance comprises a stoma seal urged towards the stomal aperture of the wafer for sealing against a stoma in use, the stoma seal comprising a first seal wall and a second seal wall, the second seal wall having a seal-contact aperture therein, and the first seal wall having a stoma contact face for contacting a stoma, in use, through the seal-contact aperture of the second seal wall, the second seal wall being configured to shield the first seal wall to obstruct the first seal wall adhering to said exposed adhesive surface portion of the adhesive accessories.

28. The combination of claim 27, wherein the adhesive accessories is an hydrocolloid cohesive seal which can be molded and shaped to create a close contact to stoma and to protect the peristomal skin.

29. The combination of claim 27, wherein the adhesive accessories is an adhesive powder.

\* \* \* \* \*